(12) United States Patent
Holmström (10) Patent No.: US 6,321,101 B1
(45) Date of Patent: Nov. 20, 2001

(54) METHOD AND DEVICE FOR DETERMINATION OF CONCENTRATION

(75) Inventor: Nils Holmström, Järfälla (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/529,842

(22) PCT Filed: Oct. 20, 1998

(86) PCT No.: PCT/SE98/01877

§ 371 Date: Apr. 19, 2000

§ 102(e) Date: Apr. 19, 2000

(87) PCT Pub. No.: WO99/22230

PCT Pub. Date: May 6, 1999

(30) Foreign Application Priority Data

Oct. 29, 1997 (SE) .................................................... 9703958

(51) Int. Cl.[7] ............................ G01N 27/00; A61N 1/365
(52) U.S. Cl. .......................... 600/345; 600/309; 600/364; 600/347; 607/22; 204/406; 204/416
(58) Field of Search .................................. 600/309, 322, 600/323, 324–328, 333, 336, 345, 347, 353, 364, 365; 607/17, 22; 204/431, 416, 403, 406

(56) References Cited

U.S. PATENT DOCUMENTS

| | | |
|---|---|---|
| 3,260,656 | 7/1966 | Ross et al. . |
| 4,269,684 | 5/1981 | Zick . |
| 4,602,637 | 7/1986 | Elmqvist et al. . |
| 4,611,604 | 9/1986 | Botvidsson et al. . |
| 4,701,253 | 10/1987 | Ligtenberg et al. . |
| 4,779,618 | 10/1988 | Mund et al. . |
| 4,853,091 | 8/1989 | Mund et al. . |
| 5,562,815 | 10/1996 | Preidel . |
| 5,806,517 | * 9/1998 | Gerhardt et al. ................. 128/635 |
| 5,928,155 | * 7/1999 | Eggers et al. .................... 600/526 |
| 6,013,029 | * 1/2000 | Korf et al. ....................... 600/363 |

OTHER PUBLICATIONS

"Oxygen Pressure as Biosensor for Rate Adaptive Cardiac Pacing," Carlsten et al., PACE, vol. 17, Nov. 1994, pp. 1939–1943.

* cited by examiner

*Primary Examiner*—Kennedy Schaetzle
(74) *Attorney, Agent, or Firm*—Schiff Hardin & Waite (57) ABSTRACT

In a method and a device for electrochemical determination of the concentration of at least one dissolved chemical entity in a liquid medium, a measurement voltage U is impressed on a working electrode, in contact with the liquid medium, relative to a counter electrode, thereby causing the dissolved chemical entity to react by oxidation or reduction at the working electrode, producing a measurement evoked current. The measurement evoked current is compared to a predetermined value, and the measurement voltage U is adjusted so that the measurement evoked current is substantially equal to the predetermined value, and thus remains substantially constant during measurements. A difference $\Delta U = U - U_{min}$ is formed, which corresponds to an oxidation/reduction reaction at the working electrode, with $U_{min}$ being a minimum voltage selected as a reference level. This difference is used to calculate concentration variations of the chemical entity in the liquid. A therapy administering apparatus, such as a medical implant such as a pacemaker or the like, can be controlled dependent on the calculated concentration variations.

9 Claims, 8 Drawing Sheets

Sensor Rate: $SR = K3 \cdot \dfrac{U - Umin}{Umax - Umin}$

METHOD AND DEVICE FOR DETERMINATION OF CONCENTRATION

The present invention relates to a method for electrochemical determination of the concentration of at least one dissolved chemical entity in a liquid medium by means of a working electrode and a counter electrode, an apparatus for performing the method, an active implant containing such an apparatus and the use of such a method in an active implant such as a pacemaker or the like.

DESCRIPTION OF THE PRIOR ART AND RELATED SUBJECT MATTER

In the description the following expressions are intended to have the following meaning:

Measuring Potential: the applied potential, as related to a reference potential, during the measurement. in the description denoted E. corresponding to a Measuring Voltage: used in algorithms. which are part of the present invention in the description denoted U.

Floating Potential: the potential, as related to a reference potential, an electrode will acquire when placed in an electrolyte and no current is allowed to pass through an outer circuit, i.e. not passing through the electrolyte, in the description denoted $E_0$.

Chemical Entity: a chemical entity is defined for the purpose of this application as either a gas or a chemical substance or compound dissolved in a liquid medium.

Such entities can be subjected to analysis by electrolytic reduction/oxidation reactions and the corresponding reduction/oxidation potential, or rather the electric current evoked by said potentials for characterizing the amount and substance reduced/oxidized.

Working Electrode: herein and below relates to the electrode at the surface of which the reduction of the chemical entity takes place, e.g. the working electrode can be used as an oxygen-sensor.

Sensor Rate: A calculated rate increase to be added to a basic pacing rate when the sensor is used in an active implant. The sensor herein and below being an oxygen sensor comprising a working electrode and a counter electrode and optionally a reference electrode.

A chemical entity is defined for the purpose of this application as either a gas, a chemical compound or substance dissolved in a liquid medium, said entities to be reduced or oxidized under the influence of an electric potential applied between electrodes.

Such entities can be subjected to analysis by electrolytic reduction/oxidation reactions and the corresponding reduction/oxidation potential, or rather the evoked electric current for characterizing the amount and substance reduced/oxidized.

In modern medicine, implantable heart pacemakers are used increasingly for the therapy of heart arrhythmia. It is a well-know fact that physical demands on the body requires levels of oxygen adapted to the degree of physical activity to be delivered to the body. Thus the body activity lowers the venous oxygen concentration in the blood as a function of the degree of activity. The oxygen concentration in the blood and the changes in the concentration may be used as an indicator for a change in the stimulation pulse rate in order to regulate the rate of the stimulation pulses emitted by the pacemaker. See Pace, Vol. 17, p1939–1943, Johan Carlsten et al.

It is to be noted that oxygen in the blood exists in an equilibrium, The greater part of the oxygen is attached to the hemoglobin molecules while the some part is dissolved in the blood plasma and transported thus through the vascular system including the heart. The amount of oxygen combining with the hemoglobin is dependent on the oxygen's partial pressure in the blood, measurements of either one will give indication as to the amount of oxygen present. There are also other factors, which govern the ability of hemoglobin to combine with the oxygen, such as temperature and pH.

The oxygen saturation of the blood, which is a measure of the amount of oxygen bound by the hemoglobin, may be measured by different methods, e.g. transmission photometry and reflection photometry in the venous blood or measured indirectly by electrochemical methods, see above.

The photometric measurements do not show a linear dependency on the oxygen saturation and the measurement values have to be compensated in various ways, which is not the case in the electrochemical methods for measuring the oxygen partial pressure. In these later methods there is a linear dependency in the measurements of the measured current/measured voltage as a function of the oxygen partial pressure.

The measurements using electrochemical methods make use of the fact that the oxygen molecules dissolved in the blood are chemically reduced on the surface of the working electrode when the potential during a measurement pulse is forced to negative potential (about 1 volt) relative to a reference electrode/potential. The counter electrode is below assumed, at least partly, to have a surface made from carbon. In the reduction process, hydroxide ions are produced and the amount of these ions are dependent on the concentration of dissolved oxygen according to the reactions:

at the working electrode $2\ H_2O + O_2 + 4e^- \rightarrow 4\ OH^-$ at the counter electrode $4\ OH^- + C \rightarrow CO_2 + 2\ H_2O + 4e^-$ The above equations show a simplified picture of the process in the liquid (electrolyte), but for the purpose of this description they are sufficient.

The electrical current flowing through the liquid medium to the working electrode WE during the measurement pulses is carried by the hydroxide ions. This current called the oxygen current ($I_{pO2}$), is proportional to the amount of hydroxide ions formed on the working electrode surface. During the measurement pulse the carbon coating of the counter electrode is oxidized to minute amounts of carbon dioxide ($CO_2$), which is removed by the blood stream.

United States patents disclosing different aspects of electrochemical measurement teachings are e.g. U.S. Pat. Nos. 4,602,637 and 4,611,604 and 4,779,618 and 4,853,091. A factor influencing these measurements is the drift of the reference electrode.

One of the more stable reference electrodes that may be used is the Ag/AgCl-electrode. However, the bio-compatibility of the reference electrode is important as the reference electrode is to be implanted. Other types of reference electrodes with better bio-compatibility are not as stable as the Ag/AgCl-electrode. The Ag/AgCl-electrode also must be protected by e.g. a membrane when used in vivo because of the above reason.

During testing of electrodes it has been observed that the measured oxygen current (the current depending on the voltage imposed on the working electrode) increases or decreases by time.

SUMMARY OF THE INVENTION

It is therefore a principal object of the present invention to improve the certainty in the measurements and to eliminate the uncertainties emanating from the possible drift over time of the potential of the reference electrodes used in the prior art.

It is also a purpose of the present invention to improve the sensitivity of the oxygen/working electrode by diminishing the influences of the drift of the reference electrode by making it possible to perform the measurements without a reference electrode.

Another object is the possibility of using a measuring current that will be in a range most preferred for the reaction of the oxygen at the working electrode, i.e. where the sensitivity of the measurements is optimal.

Yet another object is to reduce as much as possible the amount of energy used for the measuring pulses and still make certain that a relevant value is attained.

The above objects are achieved in accordance with the principles of the present invention in a method and in a device for electrochemical determination of a concentration of at least one dissolved chemical entity in a liquid medium, employing a working electrode and a counter electrode with a measurement voltage being impressed on the working electrode relative to the counter electrode, the dissolved chemical entity reacting by oxidation or reduction at the working electrode with the reaction producing a measurement evoked current, and wherein the measurement evoked current is compared with a predetermined value and the measurement voltage is adjusted, dependent on this comparison, by an amount so that the measurement evoked current is substantially equal to the predetermined value, so that the measurement evoked current is at a substantially constant value during the measurement, and wherein a voltage difference is formed which corresponds to an oxidation/reduction reaction at the working electrode and this difference voltage is used to calculate concentration variations of the chemical entity in the liquid.

It has thus, according to one embodiment of the invention, been found that there is a possibility to exclude the reference electrode, i.e. the measurements can be performed using a minimum of only two instead of three electrodes.

DESCRIPTION OF THE PREFERRED EMBODIMENT

Figure 1:
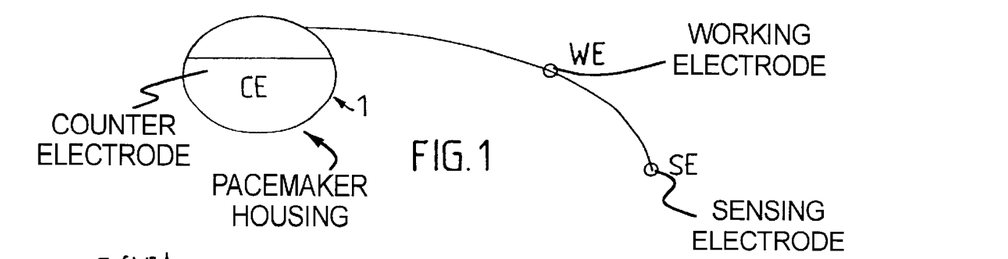
FIG. 1 is a generalized illustration of an implant utilizing the invention.

The heart pacemaker system shown schematically in FIG. 1 consists of a pacemaker, where the housing 1 or portion thereof functions as the counter electrode CE of the system attached to the housing 1 is an electrode lead having a working electrode WE, and a stimulating/sensing electrode SE. This is of course a very simple setup comprising only the necessary components to measure the oxygen pressure in the blood stream through the heart and to effect stimulation from the pacemaker as a response to the measurements made by the oxygen sensor.

The pacemaker making use of the method according to the invention is provided with means for carrying out the measurements and means for sensing and pacing of the heart as well as control means for controlling the pacing (stimulation rate) in dependence of the made measurement and in accordance with the need of the patient.

The measurements may be performed at intervals and may be synchronized either with set rate or in response to different inputs to the pacemaker. e.g. sensed signals etc. or chances in the same. This means that the measurements need not be performed in each heart cycle, although the mean time between measurements should be constant.

The method herein is described as if a single measurement of the current is made during the measurement pulse. However, in order to compensate for especially the double layer capacitance of the electrode the usual procedure is to integrate at least a part of the current caused by the measuring pulse over time and actually use this value for the control of the applied measurement potential.

In the preferred embodiment described below use is made of a double potential step technique.

However, the algorithms used in the method according to the invention may also be applied to the single potential step technique.

Figure 2:
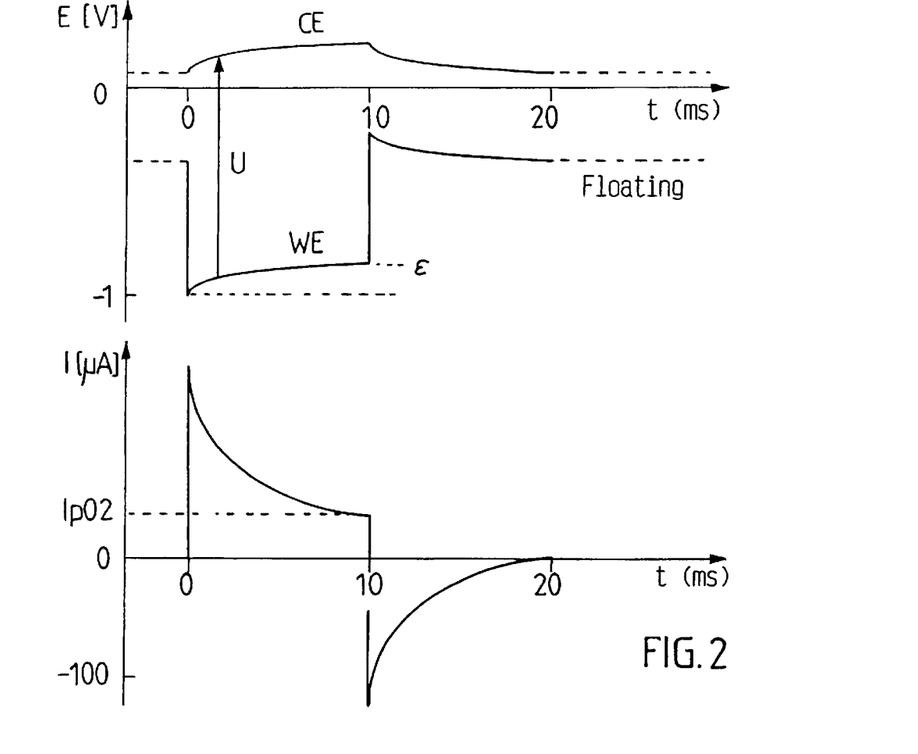
FIG. 2 shows a double-step measurement pulse and the resulting current in a preferred embodiment of the invention.

In the double potential step technique the measurement pulse consists of two phases lasting about 10 ms each. A first phase in which the impressed voltage between the working electrode WE and the counter electrode is approximately −1 V and a second phase where the impressed voltage is equal in step but having the opposite sign. This is illustrated in FIG. 2, the upper diagram. The potentials, versus a fictive reference electrode of the counter electrode CE and the working electrode WE are shown as related to a fictive reference electrode. It should be noted that in this embodiment there is no reference electrode and the figure has been drawn to show the relation between the voltage on the counter electrode and the working electrode in relation to each other. The potential of the reference is of no consequence in this case. It is only important that the potentials differs so much that there will be an reaction of the oxygen at the working electrode. Before and after the measurement pulse the potential of the counter electrode and the working electrode WE are in a floating state. The double layer capacitance of the counter electrode surface will acquire the potential increase "ε" during the measurement pulse. Because the voltage between the two electrodes (WE–CE) is kept constant the potential of the working electrode will show the corresponding change in potential. If the area of the counter electrode CE, compared to the area of the working electrode for instance exhibits a surface ratio of more than 100:1 the error "ε" will then be negligible. The error "ε" de facto is the result of the charging of the counter electrode.

In FIG. 2, the lower diagram, the resulting current I from the counter electrode CE to the working electrode WE during the measurement pulse is shown. The first part of the pulse in the first step shows the effect of the charging of the double layer at the working electrode and at the end of the pulse remains only the part of the current due to the oxygen current $I_{pO2}$, i.e. the current resulting from the reduction of oxygen. In the second step only the effects of the double layer is present.

During the first phase oxygen present in the medium (the blood in the heart in this case) is reduced on the surface of the working electrode as a result of the impressed voltage giving rise to a current. The first phase and the second phase should be understood as two parts of the measurement cycle. In between the cycles the working WE and the counter electrode CE will be at floating potentials $E_{WE-float}$ and $E_{CE-float}$, respectively.

The basic feature of the method is to set a predetermined current $I_{set}$ to be attained during the measurement, since the quality of the measurement is dependent on the sensitivity of the measurements.

Figure 3:
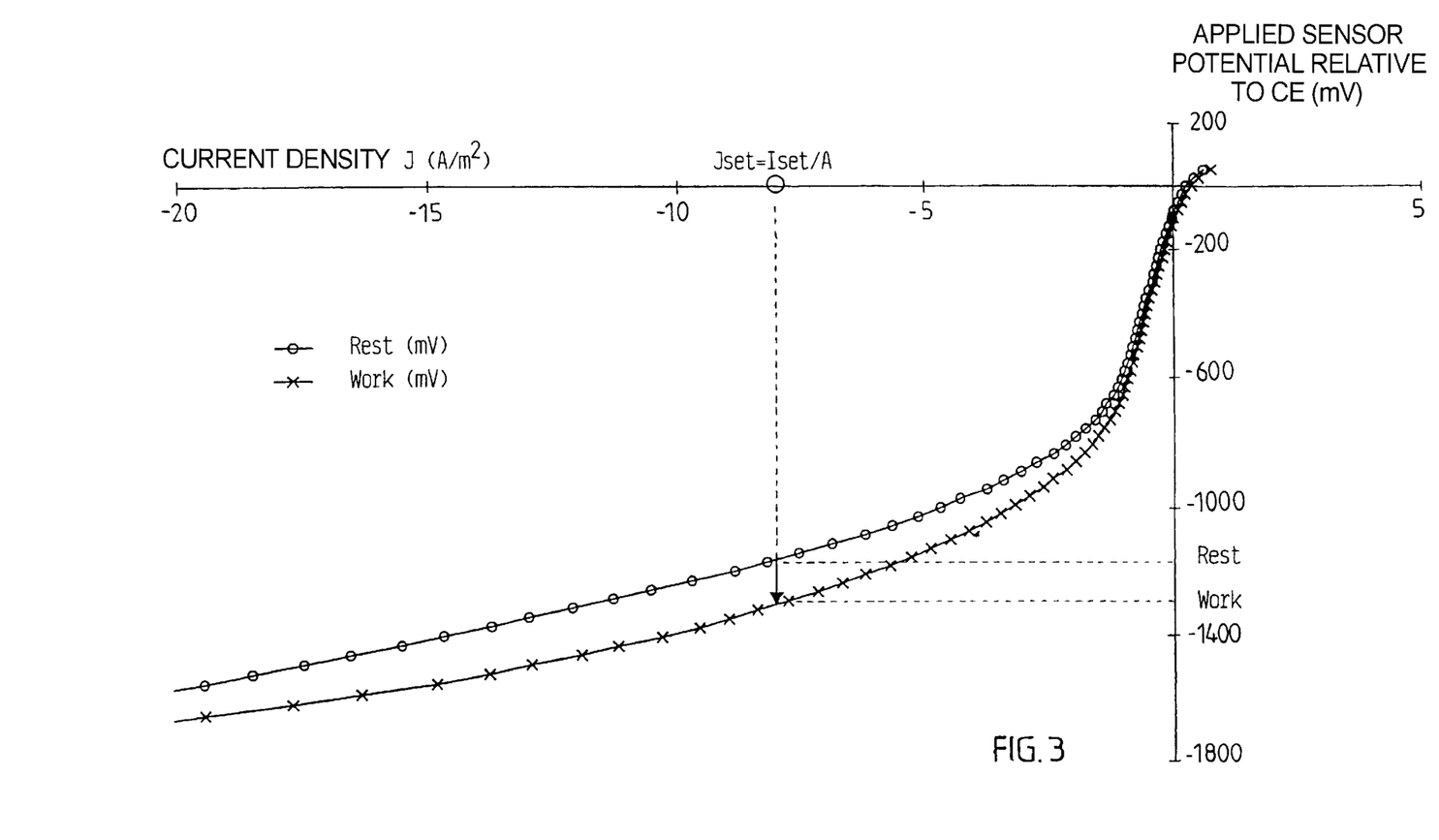
FIG. 3 shows the components of a test system for illustrating the measurements in accordance with the inventions.

In FIG. 3 a test system for carrying out the invention is shown. The system comprises a personal computer, a step potentiostat and an electrochemical cell having a counter electrode CE and a working electrode WE.

Figure 4:
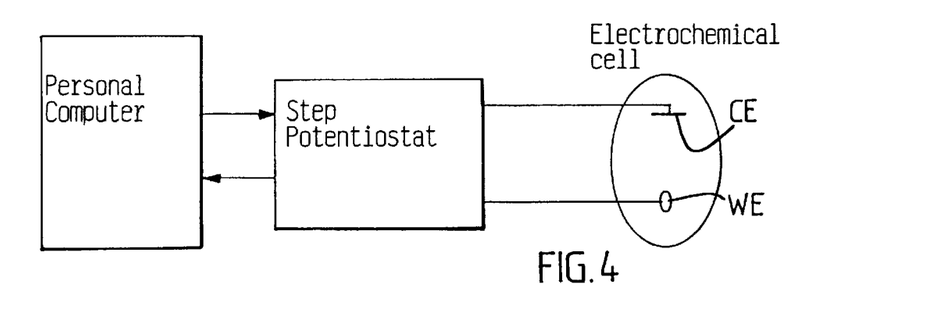
FIG. 4 shows a voltage-time diagram with a double potential step in accordance with the invention.

In FIG. 4 a double potential step voltammogram showing the applied sensor potential WE–CE in mV at "rest" (denoted) and "work" (denoted ) respectively, vs. the achieved J being the current density in A/m². The measurements were made in a cell containing Ringer solution of 37° C. temperature and having gas mixtures of 6% or 2% oxygen, 6% carbon dioxide and nitrogen bubbled through the cell using a working electrode and a counter electrode. The electrode material in this example was pyrolytic carbon with 10% Silicon (SJM St. Jude Medical Carbon).

In this example the voltage difference at 6% and 2% O2 (rest and work) is almost constant from about 6 to 16 A/m², which means that the current $I_{set}$ is not critical for the function and variations of $I_{set}$, i.e. fast variations of oxygen pressure do not hazard the measurement. The floating voltage for the working electrode WE and the counter electrode CE may vary slowly by time. This means that the voltage curves in FIG. 4 are displaced up- or downwards. The difference between the two curves at rest and work will, however, stay the same at a given $I_{set}$.

Also may be noted that when the current decreases the oxygen sensitivity also decreases because the reduction potential comes closer to the limit for the reduction to take place. On the other hand if the current increases by time the measurement pulse amplitude will have to be reduced since otherwise the risk for tissue stimulation is obvious. Also in this case the sensitivity decreases with the increasing current.

The method according to the invention will be described in conjunction with FIG. 5, which shows the voltage vs. time diagram, U being the voltage generated to achieve a constant set current. $I_{set}$, at all oxygen concentrations, and $U_{min}$ being a slowly varying reference (calculated) voltage in a control program $U_{min}$ is set as an initial value in the algorithm used in the method and adjusted as explained below. The difference between U and $U_{min}$, called ΔU, is used as a measure of the relative oxygen pressure in the medium/blood.

If during the measurement the evoked current $I_{pO2}$ being the current resulting from the reduction of oxygen is higher than $I_{set}$, the voltage U at which the measurement takes place is incrementally reduced with an amount dU before the next $pO_2$-measurement. Likewise, if the current is below $I_{set}$, the voltage U is incrementally increased with an amount dU. On account of the measurement potential quickly being adjusted, the measurement current will always be close to $I_{set}$, i.e. the average current from the counter electrode or the case CE will be constant. This makes the potential of the case vs. the fictive reference electrode a constant or a potential which by time slowly increases in a predictable way. This is especially true if the case has a carbon surface which oxidizes to carbon oxide at anodic load which will change the physical appearance of the case, and thus would normally influence measurements.

The voltage between the case and the sensor during a measurement, called the measurement voltage U will hence vary with the variations in the oxygen pressure, and this voltage is used as a measurement variable . At low oxygen pressure the voltage U will have to be increase and at high oxygen pressure the voltage U will have to be decreased in order to keep the current stable and close to the $I_{set}$-value.

The reason behind this is, that in the method according to the invention, the current through the measuring unit, described in connection with the description of FIG. 4, is kept as near constant as possible by controlling the voltage over the oxygen sensor, e.g. the cell comprising the working electrode and the counter electrode. However, in the medium/blood, as is described in this example, the impedance through the cell(measuring unit) is dependent on the amount of oxygen able to react at the working electrode WE. (at that specific voltage range) When the oxygen pressure is low (a lack of oxygen exists) there will be less oxygen available at the WE than when the oxygen pressure is high (no lack of oxygen). That is, a lack of oxygen will require a higher voltage U over the cell in order to keep a set $I_{set}$.

$U_{min}$ actually corresponds to the voltage measured when the person, carrying the implant, is at rest, i.e. when the oxygen pressure is at its peak. This voltage $U_{min}$ is subtracted from the measured value U and the difference is used to calculate relative oxygen pressure present and the appropriate increase in the stimulation frequency, the sensor rate.

As we have described above $U_{min}$ changes over time. One reason is that $U_{min}$ is influenced by how much the double layer of the counter electrode CE is charged during several consecutive measurement pulses. Therefore $U_{min}$ will have to be adapted to these variations, i.e. the value of $U_{min}$ has to be changed by an amount $dU_{min}$.

Figure 5:
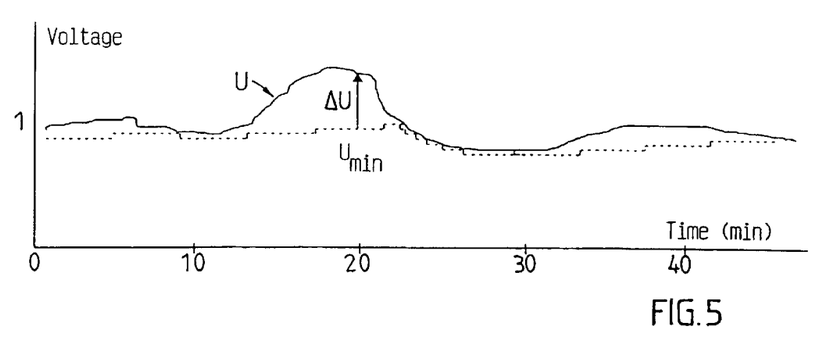
FIG. 5 is a diagram relating the measuring potential U and the potential $U_{min}$, which represents the potential of the working electrode at rest or at a highest oxygen pressure and which is a value calculated from the measurements in accordance with the invention.

This procedure is illustrated in FIG. 5. In FIG. 5 the cell voltage U, i.e. the measurement voltage U is denoted by a solid line and $U_{min}$ is denoted by a broken line. In the method it is assumed that the voltage Of $U_{min}$ is slowly increasing and thus the reference voltage $U_{min}$ is increased with one step $dU_{min}$, (1 mV<dU<20 mV) after a relatively long time interval (10 min<Tg<24 h). If after the increase the difference $\Delta U = U - U_{min} < 0$ the measurement voltage $U_{min}$ is decreased with $dU_{min}$ immediately, and in time for the next measurement pulse. If the difference $\Delta U = U - U_{min} > 0$ the measurement voltage $U_{min}$ is increased with $dU_{min}$ after a predetermined time interval Tg, (10 min<Tg<24 h). Preferably the decrease in $U_{min}$ is effected at a faster rate than the increase in the same. Thus can be seen in the figure that the according to the diagram the "patient" is at work at a time around 18 min., while relatively at rest before and after that time period. What actually was done in this case was changing the concentrations in the test system according to FIG. 4.

With this arrangement the value of $\Delta U = U - U_{min}$ will always have a value around zero at rest. The magnitude of the same parameter mirrors the oxygen pressure without the use of a separate reference electrode.

Figure 6:
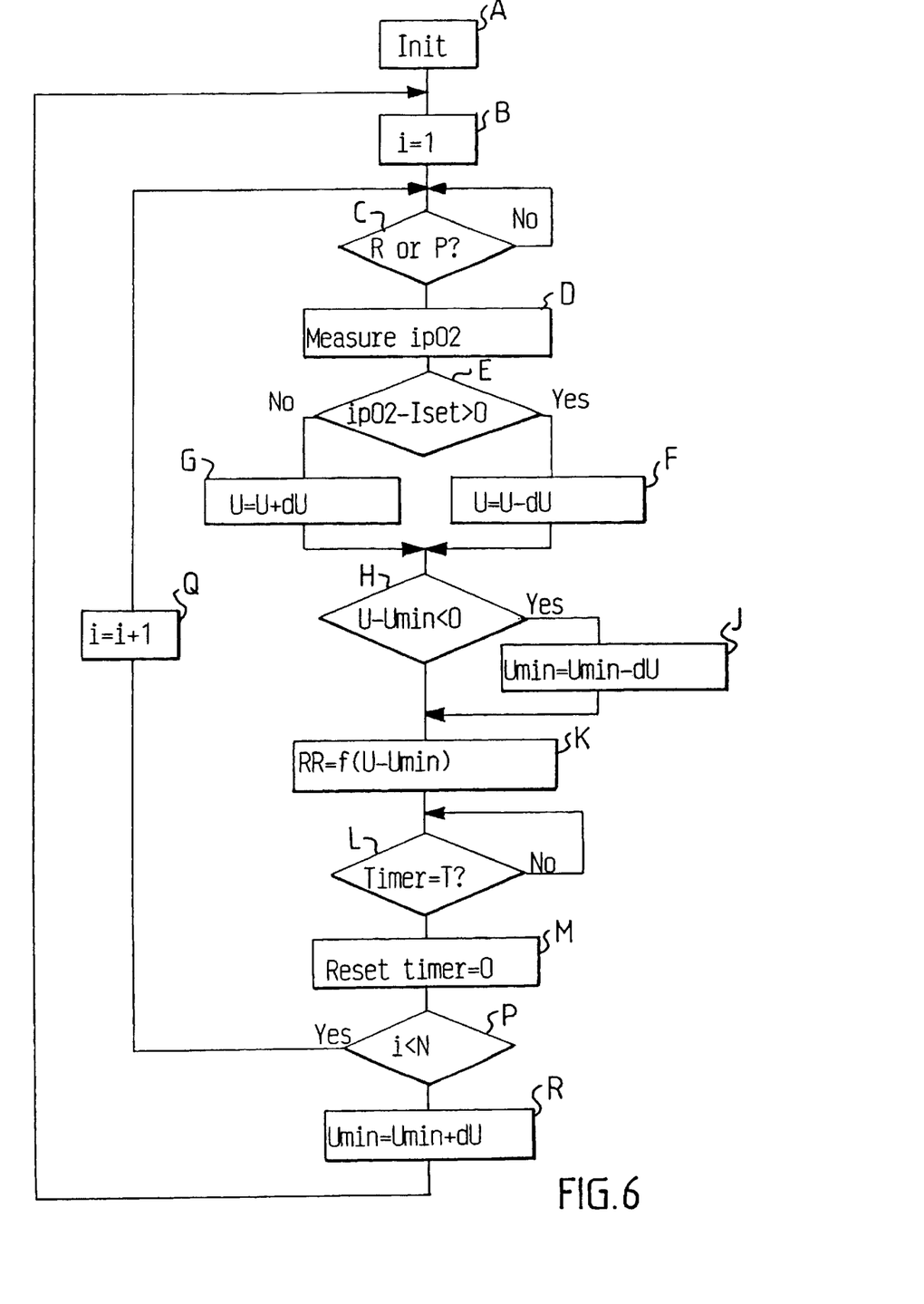
FIG. 6 is a flow diagram for an embodiment of the inventive method.

A first flow chart showing an example of how to implement a first embodiment of the procedure of the measurements according to the invention in a device is shown in FIG. 6

In block A of the flow chart (FIG. 6) the initial values for the procedure are set E.g. the following values may be used: The measurement current $I_{set}$ is set to 50 $\mu$A, a time constant T is set to 1.5 sec., the measurement voltage U is set to 800 mV, an incremental step dU is set to 10 mV and $U_{min}$ is set to 800 mV, an incremental step in the $U_{min}$ is set to 15 mV and the number of cycles N is set to 100. The chosen values for $I_{set}$, U, dU, $U_{min}$ and $dU_{min}$ depend on the type of working electrode used and are chosen accordingly. In this example the working electrode is a gold electrode having a surface area of app. 7,5 mm².

In block B a counter "i" is set to "1".

Decision box C represents a waiting loop used for synchronizing the measurements to some event in the heart, e.g. an atrial or ventricular stimulation pulse, a P-wave or a QRS-complex, for the measurements. The decision box asks if the specified event has occurred. The loop through decision box C is executed until "R or P?" is set to "true", i.e. the specified event has occurred.

In block D the calculation of the $l_{pO2}$, i.e. the oxygen dependent current arising from the reaction of the oxygen at the working electrode WE, is performed by applying the measurement potential U.

In decision box E is determined if $I_{pO2}-I_{set}>0$. If this is true the measurement voltage will be decreased with dU in block F, if not U will be increased with the dU in block G. From block F and G the procedure continues in decision box H in which it is determined if $U-U_{min}<0$. If this is true, the voltage $U_{min}$ is decreased in block J with an amount $dU_{min}$. The procedure is continued in Block K.

Returning to decision box H, and in case the statement $U-U_{min}<0$ is false, the procedure is continued in block K.

In block K a rate increase is calculated according to the formula $SR=f(U-U_{min})$, in which "f" represents a function which may be programmable.

Thereafter in block L, which represents a waiting loop "Timer=T?", which will be run through until the time for the next measurement is up, i.e. Timer is equal to T. Timer will then be set to "0" and in decision box P it is checked whether "i<N". If that is not the case "i" will be set to "i=i+1" and return will be made to decision box C.

If, however, the counter "i" equals N in block P then in block R, $U_{min}$ will be set to $U_{min}+dU_{min}$ and return will be made to block B and the measurement cycle will be repeated Other initial values may of course be applied e.g. U may be chosen higher and will fast adjust itself to a value close to the approximate level for the measurements and to give the predetermined $I_{set}$. $I_{set}$ shows for ice a dependency of the used electrode and thus $I_{set}$ should preferably be a programmable value.

Figure 7:
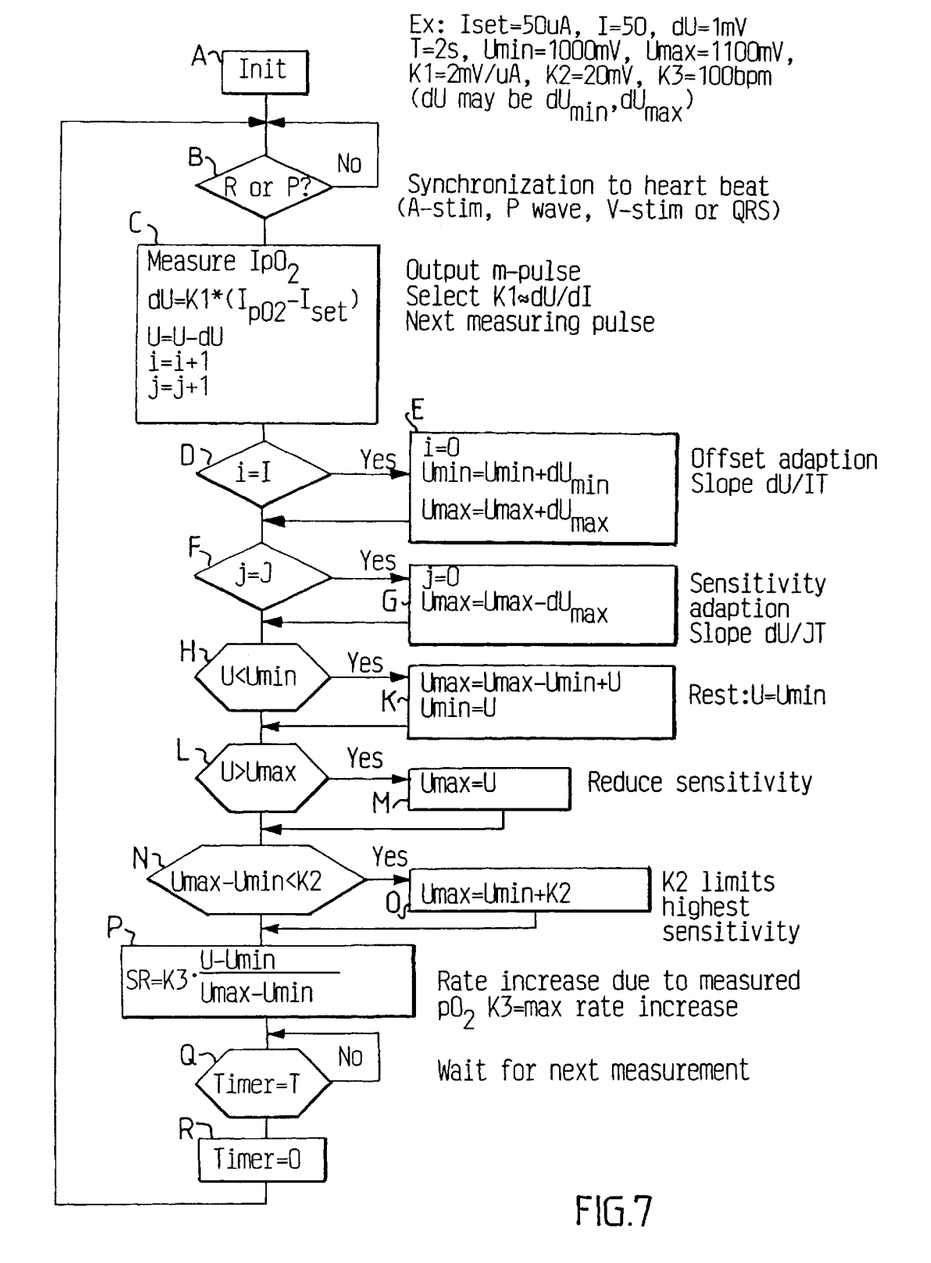
FIG. 7 is a flow diagram for another embodiment of the inventive method.
Figure 8A:
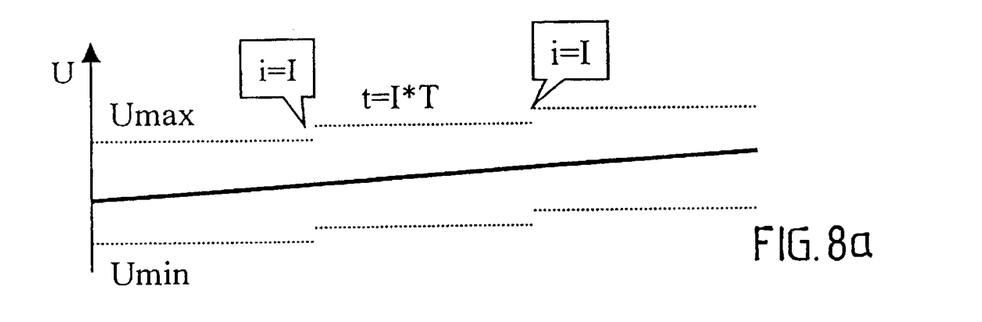
FIGS. 8a through 8d respectively show diagrams illustrating adjustment loops in the embodiment of the method shown in FIG. 7.
Figure 8B:
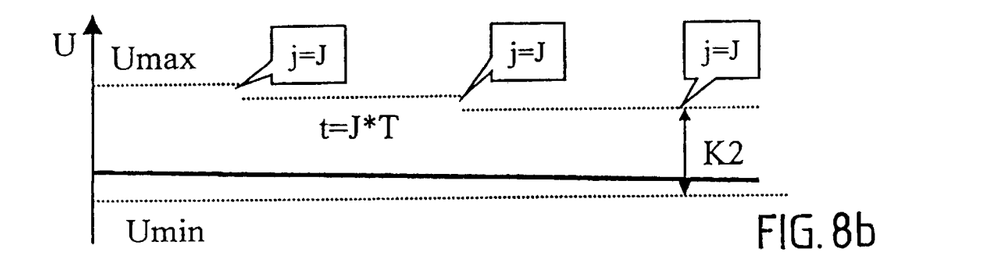

A second embodiment of the method according to the invention is presented in connection with FIG. 7, and FIGS 8a–8b.

The value of dU may also be set separately, which means that in block E and block G the values may be set as $dU_{min}$ and $dU_{max}$ as indicated in the figure. They may however all be set to the value dU as above.

A second flow chart showing a second embodiment of how to implement the procedure of the measurements according to the invention in a device is shown in FIG. 7.

In block A of the flow chart (FIG. 7) the initial values for the procedure are set. E.g. the following values may be used: The measurement current $I_{set}$ is set to 50 $\mu$A, number of iterations I=50, J=150, a time constant T is set to 2 sec., variable limits for the measurement voltage $U_{min}$ is set to 1000 mV and $U_{max}=1100$ mV, a factor K1 limiting the incremental step dU is set to 2 mV/$\mu$A, a factor K2 which limits the highest sensitivity of the measurements is set to 20 mV and K3 a factor which limits the highest rate increase is set to 100 bpm.

The value of dU may also be set separately, which means that in block E and block G the values may be set as $dU_{min}$ and $dU_{max}$ as indicated in the figure, they may however all be set to the value dU as above.

Decision box B represents a waiting loop used for synchronizing the measurements to some event in the heart e.g. an atrial or ventricular stimulation pulse, a P-wave or a QRS-complex, for the measurements. The loop through decision box B is run executed until "R or P?" is set to "true", i.e. the specified event has occurred.

In block C the measurement of $l_{pO2}$ is performed by applying the measurement potential U, i. e. the oxygen dependent current arising from the reaction of the oxygen at the working electrode WE. A value $dU=K1*(I_{pO2}-I_{set})$ is calculated and the next measurement voltage is calculated as U=U−dU, and counters "i" and "j" are set to "1". K1 is a constant which is chosen to be approximately equal to the derivate for the curve shown in FIG. 3 at $I_{set}$.

In decision box D it is checked whether "i"=I, if it is, progress is made to block E in which "i" is set to "0", $U_{min}$ is set to $U_{min}+dU_{min}$ and $U_{max}$ is set to $U_{max}+dU_{max}$. This represents an offset adaptation i.e. an adaptation to the measurement voltage U as shown in 8a (described below). Thereafter progress is made decision box F.

If in decision box D "i" is not equal to "I", then progress is made decision box F.

In decision box F it is check whether j=J, if it is, progress is made to block G in which "j" is set to "0", $U_{max}$ is set to "$U_{max}-dU_{max}$". This represents a sensitivity adaptation i.e. giving a narrower window for U. The window is limited by $U_{max}$ and $U_{min}$ as shown in FIG. 8b (described below). Thereafter progress is made to decision box H If in decision box F "j" is not equal to "J", then progress is made to decision box H.

Figure 8C:
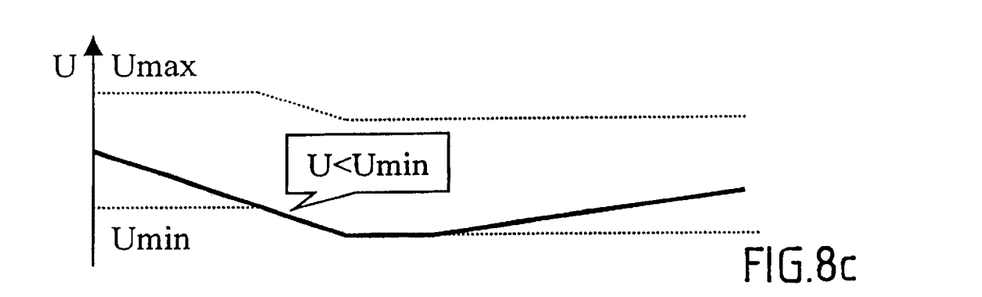

In decision box H it is checked whether $U<U_{min}$, if it is, progress is made to block K in which $U_{max}$ is set to $U_{max}-U_{min}+U$ and $U_{min}$ is set to U (this happens when the measurement U goes below the lower limit of the voltage window as shown in FIG. 8c (described below), thereafter progress is made to decision box L.

If in decision box H, the measurement U is not below $U_{min}$ then progress is made directly to decision box L.

Figure 8D:
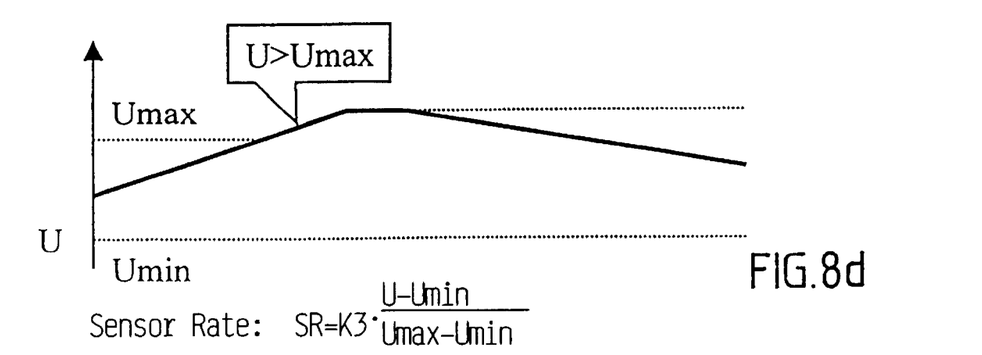

In decision box L it is checked whether $U<U_{max}$, if it is, progress is made to block M, in which $U_{max}$ is set to U (this happens when the measurement U surpasses the upper limit of the voltage window as shown in FIG. 8d (described below),) thereafter progress is made to decision box N.

If in decision box L, the measurement U is not below $U_{max}$ then progress is made directly to decision box N.

In decision box N is checked whether "$U_{max}-U_{min}<K2$, where K2 is a constant, set initially. If so the voltage window is increased window by adding the amount K2 to $U_{min}$ in block O (as is shown in FIG. 8d). From there progress is made to block P. If the difference "$U_{max}-U_{min}$" is equal to or greater than K2 then progress is made directly to block P In block P a rate increase SR (sensor rate) is calculated, where SR=K3*[(U−$U_{min}$)/($U_{max}$−$U_{min}$)], where K3 is a constant limiting the maximum rate increase.

Decision box Q, which represents a waiting loop, is executed until the timer is equal to "T". Then the next measurement is performed, i.e. when return is made to decision box B.

FIGS. 8a through 8d illustrate the operation of the rate algorithm on which the flow diagram of FIG. 7 is based.

FIG. 8a which corresponds to block E in FIG. 7 shows how the minimum and maximum values for the measurement voltage is stepwise adjusted to a changing measurement voltage U. $U_{min}$, which corresponds, as indicated above to the situation when the person carrying the implant is at rest, to a basic rate for the pacing and $U_{max}$, which corresponds to a maximum rate follow each other and the incremental step $dU_{min}$ and $dU_{max}$ is the same for both or are different values. This is an adjustment for a change in the measurement voltage depending on changes in the electro-chemical cell. Each stepwise change occurs when "i" is equal to "1" and the time period "t" (block E in FIG. 7.) before the next change corresponds to "I*T".

In FIG. 8b a sensitivity adaptation of the measurements is shown by a stepwise adjustment of $U_{max}$ performed after a time period "t" which equals "J*T" (block G in FIG. 7). Note that the constant K2 is marked in FIG. 8b. This is the value which is checked in block O in FIG. 7.

In FIG. 8c it is shown that when the measurement voltage U falls below the present $U_{min}$, $U_{min}$ is set equal to U (block K in FIG. 7).

In FIG. 8d it is shown that when the measurement voltage U exceeds $U_{max}$, $U_{max}$ is set to U.

Figure 9:
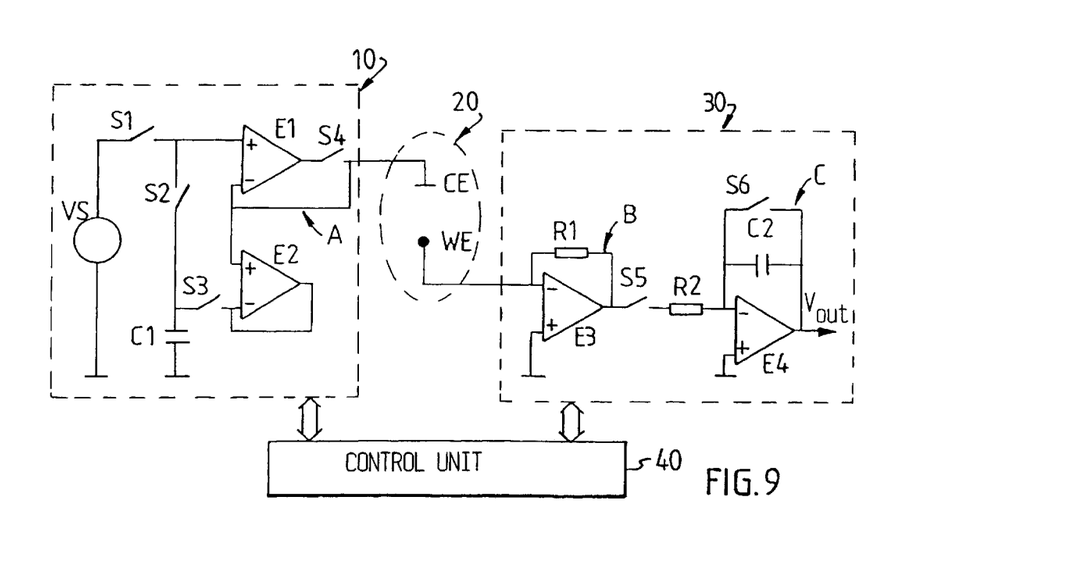
FIG. 9 is a circuit diagram of a first embodiment of a device according to the present invention.

A preferred device for accomplishing these measurements is shown in FIG. 9. The circuit diagram in FIG. 6 has three main parts. Part 10 comprises the circuitry connected with the counter electrode CE. Part 20, the electro-chemical cell comprises liquid medium (the electrolyte), the counter electrode CE and the working electrode WE. Part 30 comprises the circuitry connected to the working electrode WE. This part also comprises a current amplifier and an integrating circuit. Such devices, such as amplifiers and integrating circuits are well-know within the art and will not be further described here. The device moreover comprises a control unit 40.

Part 10 has a voltage source VS, the positive terminal of which is connected to a switch S1. The negative terminal of the voltage source VS is connected to a common ground. A capacitor C1 and a switch S2 are coupled together in series and are in parallel with the voltage source VS and the switch S1. The capacitor C1 is connected on one side to the common ground.

The non-inverting input of an operational amplifier E1 is connected to a point between the switches S1 and S2. The inverting input of the same amplifier E1 is coupled to the non-inverting input of a voltage follower E2. The output of the operational amplifier E1 is coupled via a switch S4 to the counter electrode CE and to the inverting input of E1.

The output of the voltage follower E2 is coupled via switch S3 to a point between switch S2 and capacitor C1 and to the inverting input of E2.

Part 20 includes the electrodes and the medium in which the measurements are to take place.

The working electrode WE is connected to the inverting input of a operational amplifier E3 in circuit part 30. The non-inverting input of the operational amplifier E3 is connected to the common ground. Parallel to the output of E3 and the inverting input of the same a resistor R1 of 10 k$\Omega$ is arranged. A switch S5 is connected in series to the resistor R2 (100 k$\Omega$), which is coupled to the inverting input of E4. In the negative feedback loop of E4 the capacitor C2 and the switch S6 are connected in parallel.

The sample and hold circuit is formed by this last mentioned operational amplifier E4 having the inverting input connected to R2, the non-inverted input to the common ground and a switch S6 and a capacitor C2.

The control unit 40 includes among other things a microprocessor, a ROM in which a program implementing the invention for example in the form of the processes shown as examples in connection with FIGS. 6 and 7 may be stored, a RAM for storing and calculating data from the measurements and the calculations performed, input means, such as a programmable unit to be used in conjunction with a programmer (the programmer is a separate device used for communication with the active implant) in order to set initial values for the algorithm to be executed by the program, input channels for providing measurement data to the microprocessor, and A/D-converters for conversion of analog values measured in the process to serve as input data to the stored program, output channels from the microcomputer for sending control signals to control the measurements and to the various switches to be opened and closed during the different modes of the measurements.

When the device is implemented in a pacemaker as a part thereof, the programmable unit may be integrated in the control unit for controlling the pacing parameters. Also data channels for transfer of data such as P-wave etc. indications etc. may be provided in order to use these in e.g. the rate algorithm described.

Figure 10:
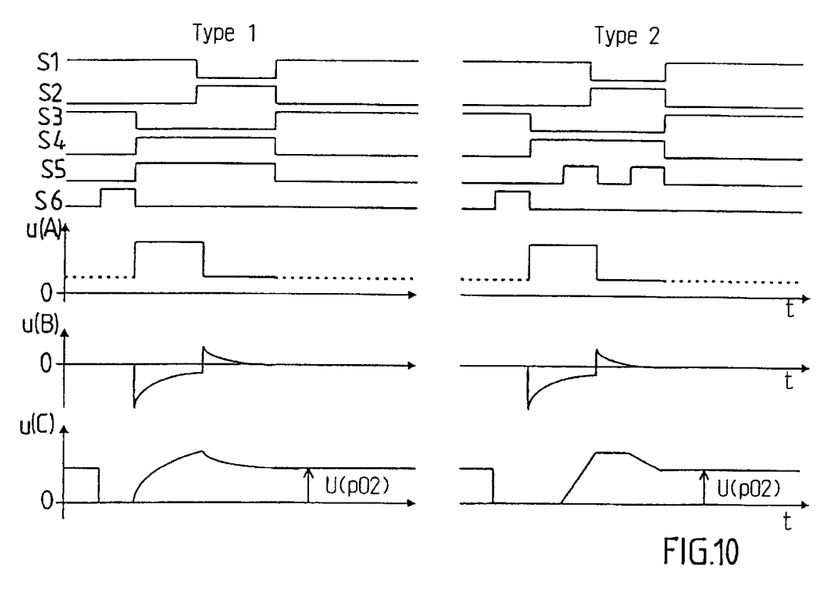
FIG. 10 illustrates switching diagrams for two types of measurement pulses relative to a time scale, and shows the resulting potentials at three locations in the device according to the present invention.

The switching diagram in FIG. 10 shows two variants of the modes for a measurement cycle of the device, and the resulting potential on the output from E2, E3, and E4 designated U(A), U(B), and U(C), resp. In FIG. 10 (Type 1) the resulting current is integrated over the whole pulse length, i.e. the two halves of the pulse and in FIG. 10 (Type 2) approx. the last half of each of the two pulse components are integrated thereby avoiding the interfering effects from possible remaining double capacitance. This is accomplished by keeping the switch S5 closed for a part of or during the whole measurement period.

In the diagrams the potential at each instant is shown. However, the resulting oxygen current is proportional to the potential and may therefore be integrated of the time to give the results in the form of an amount of electric charge.

C1 is used for storing the floating potential before the measurement pulse.

There are 4 modes as regards the setting of the switches. 1 designates that the switch is closed and 0 that it is open.

| | |
|---|---|
| Mode 1: | S1 = 1, S2 = 0, S3 = 1, S4 = 0, S5 = 0, and S6 = 0  Type 1 |
| Mode 2: | S1 = 1, S2 = 0, S3 = 1, S4 = 0, S5 = 0, and S6 = 1 |
| Mode 3: | S1 = 1, S2 = 0, S3 = 0, S4 = 1, S5 = 1, and S6 = 0 |
| Mode 4: | S1 = 0, S2 = 1, S3 = 0, S4 = 1, S5 = 1, and S6 = 0 (=mode 1!) |

-continued

Mode 1:  S1 = 1, S2 = 0, S3 = 1, S4 = 0, S5 = 0, and S6 = 0  Type 2
Mode 2:  S1 = 1, S2 = 0, S3 = 1, S4 = 0, S5 = 0, and S6 = 1
Mode 3a: S1 = 1, S2 = 0, S3 = 0, S4 = 1, S5 = 0, and S6 = 0
Mode 3b: S1 = 1, S2 = 0, S3 = 0, S4 = 0, S5 = 0, and S6 = 0
Mode 4a: S1 = 0, S2 = 1, S3 = 0, S4 = 1, S5 = 0, and S6 = 0
Mode 4b: S1 = 0, S2 = 1, S3 = 0, S4 = 1, S5 = 1, and S6 = 0

The voltage source VS in FIG. 9 generates the desired measurement potential. The value of VS can be varied by a digital-analog-converter (DAC) controlled by control means of a implantable pulse generator.

To generate a double voltage step pulse the voltage of the counter electrode just before the pulse (Mode II) is stored on capacitor C1. When the voltage follower E2, which charges C1 to the floating voltage of the CE, is disconnected by switch S3, the voltage over C1 remains. At mode 3 the positive input of E1 is connected to the voltage source VS, in mode 4 it is connected to the capacitor C1. These two voltages are sequentially imposed between the counter electrode and the working electrode. The switches S1, S2, S3 and S4 in part 10 are switched equally for both variants of integration shown in 6a and 6b, respectively. These switches generate the double potential step pulse on the counter electrode. When S4 is closed E1 is able control its output so that the inputs of E1 are equal. This is when the counter electrode CE has the same voltage as the voltage source VS. When S4 is open no current flows through the electrochemical cell.

The voltage of the working electrode WE in this system will always be equal to common ground. This is a result of the current amplifier E3, which also gives an output voltage proportional to the measurement current due to U(B)=R1*I.

Just before the measurement pulse, during Mode 2, the integrating capacitor C2 is temporarily short-circuited by switch 6, thus resetting C2 . . . Then during mode 3 the current flowing through R2, i.e. I*R1/R2, will charge the capacitor C2 to voltage due to equation. (I) below. The current is only flowing when the switch S5 is closed. For type 1 integration S5 is closed during the whole double pulse, for type 2 S5 is closed only during the end of mode 3 and 4. After the measurement pulse the is integrated current is held on the output of E4 to the next pulse (Mode 1).

$$U(C) = U(p_{O2}) = \frac{R1}{C2*R2} \int I*dt. \quad (I)$$

This voltage $U(p_{O2})$ is fed back to the control unit, as a measure of $I_{pO2}$, $I_{pO2}$ is then determined and compared to the set current $I_{set}$.

Figure 11:
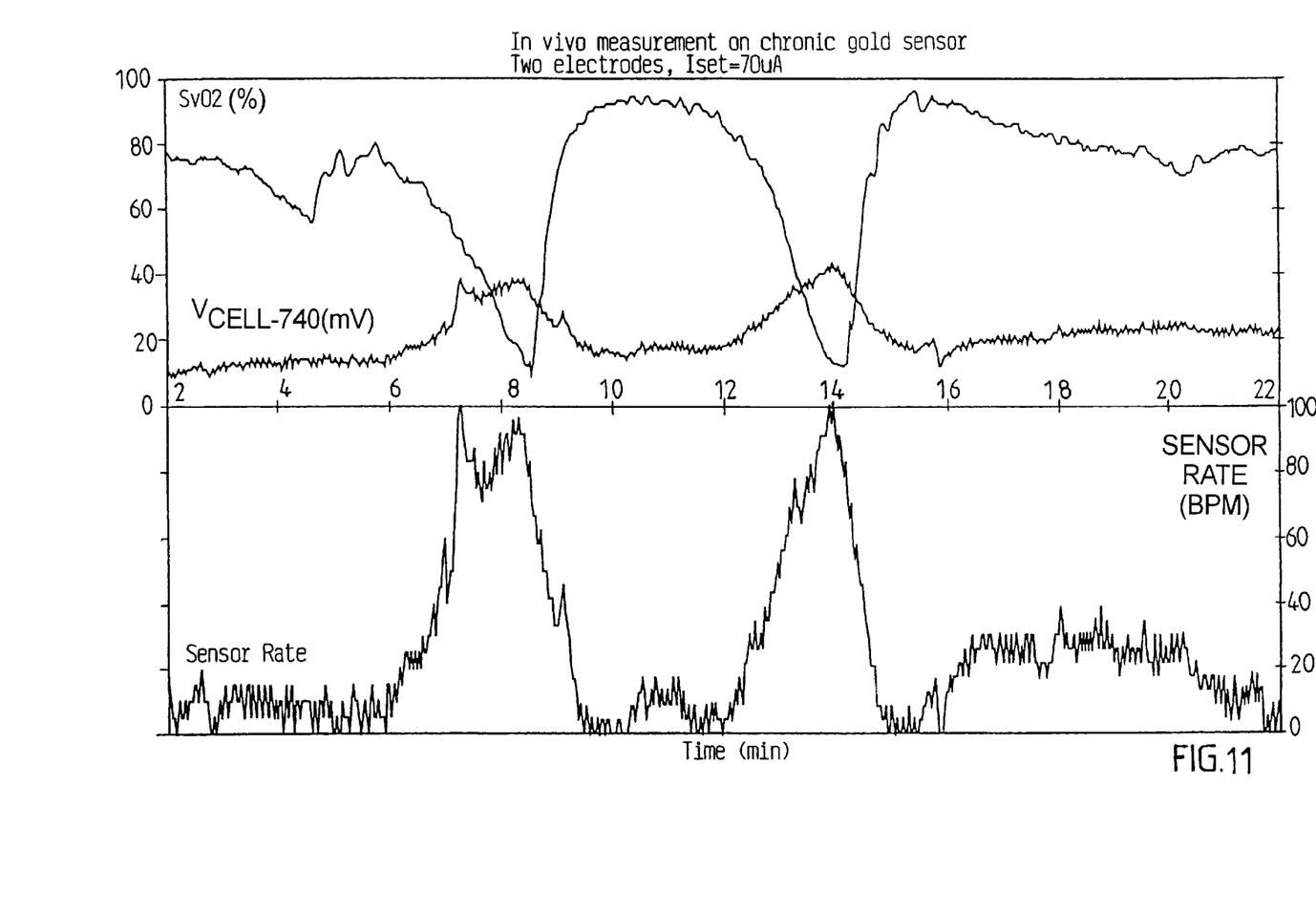
FIG. 11 shows in vivo measurements and the sensor rate obtained in accordance with the method and device of the invention.

In FIG. 11 is shown the results of in vivo measurements using the method and the algorithm and an apparatus according to this invention. The measurements were made with an pacemaker having a gold electrode, and a carbon electrode as a counter electrode. the animal was anesthesized and the blood gases were checked at regular intervals. The normal proportions of breathing gases were 50% $O_2$ and 50% $N_2O$. The differences in oxygen content in the blood were achieved by letting the breathing gases consist of only $N_2O$ for short periods of time, thus mimicking a temporary oxygen decrease in the blood corresponding to exercise or the like.

In the upper part of the diagram two curves are shown related to a time scale. The curve denoted SvO2 stands for Oxygen Measurements in Venous Blood and the other curve denoted $U_{cell}$–740 mV shows the cell voltage over the working electrode—counter electrode at a set current $I_{set}$ of 70 μA corresponding to the oxygen measurements. It can be seen that a high oxygen measurement value corresponds to a low voltage and as the oxygen measurement value decreases the voltage increases.

Below a corresponding curve is shown in which the sensor rate resulting from the measurements is shown. The correspondence between a low oxygen content in the venous blood and an increase in the sensor rate is clearly seen. At a time t≈7 can be seen that the sensor rate has been controlled by the algorithm in such a way that the sensor rate is momentarily lowered by the mechanism describe above in connection with FIG. 8d.

This may of course be accomplished in other ways. e.g. by setting a maximum sensor rate in the pacemaker itself.

The algorithms used in the methods according to the invention may of course be used together with a reference electrode also. In such a case the first step potential on the working electrode WE is related to a reference electrode and independent of the behavior of the counter electrode CE. The potential of the working electrode WE is adjusted to keep the measured I as close as possible to $I_{set}$.

Figure 12:
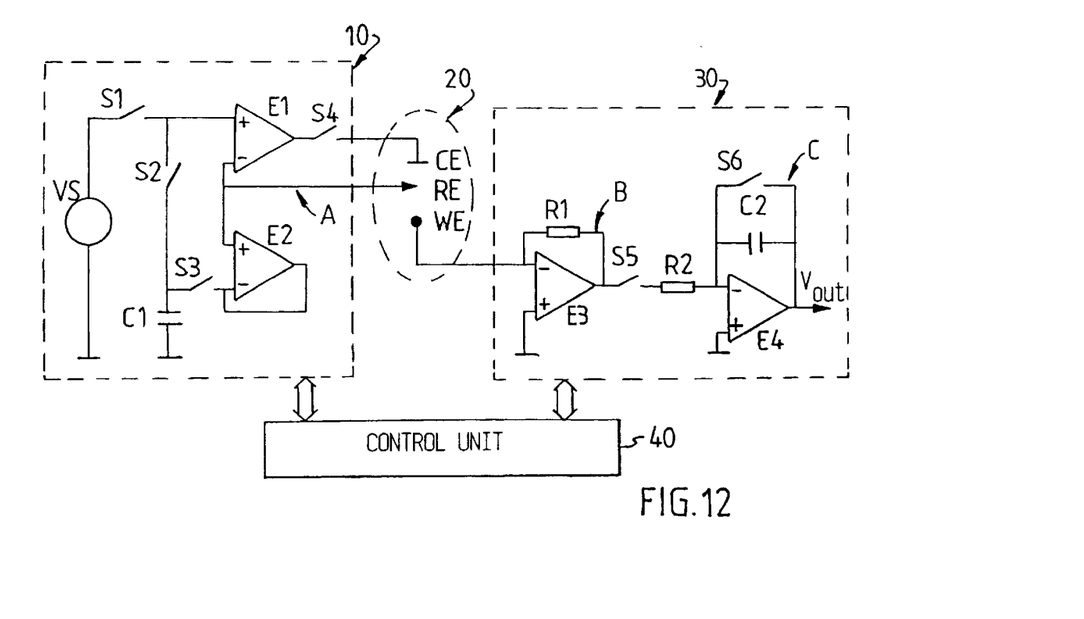
FIG. 12 is a circuit diagram of a second embodiment of a device according to the invention, wherein a reference electrode is employed.

A corresponding device is illustrated in FIG. 12 showing a reference electrode RE. All other electrodes and circuitry is the same except that the connection between the working electrode CE and the inverting input of operational amplifier E1 and non-inverting input of operational amplifier E2, respectively, no longer exists. A reference electrode RE is connect however connected to the same inverting input of operational amplifier E1 and non-inverting input of operational amplifier E2, respectively.

It is to be noted that when the device and the method according to the invention is used in an implanted pacemaker $U_{min}$ preferably is chosen to be equal to $U_{rest}$, i.e. the value a person would exhibit when in rest Preferable this value is allowed to remain set for some time period immediately after implantation and thereafter the adjustment to the pacing rate is made using the function SR (the rate adaptation provided according to the invention and exemplified in the shown algorithms).

The invention has been described in connection with the process of sensing of oxygen in blood measurements, however there is a general principle involved in the method and device, which concerns the use of only two electrodes in this type of measurements, which means that the invention as described generally applies to this kind of measurements. As has been pointed out there is a possibility to use a reference electrode as shown in connection with FIG. 12.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for electrochemical determination of a concentration of at least one dissolved chemical entity in a liquid medium, comprising the steps of:

impressing a measurement voltage U on a working electrode relative to a counter electrode, said dissolved chemical entity in said liquid being in contact with said working electrode and reacting to said voltage U by oxidation or reduction at said working electrode, resulting in a measurement evoked current;

comparing said measurement evoked current with a predetermined value;

adjusting the measurement voltage U such that the measurement evoked current is substantially equal to said predetermined value so that said measurement evoked current is substantially constant;

forming a difference $\Delta U = U - U_{min}$ which corresponds to an oxidation/reduction reaction at said working electrode, wherein $U_{min}$ is a minimum voltage selected as a reference level; and using said difference $\Delta U = U - U_{min}$ to calculate concentration variations of said chemical entity in said liquid.

2. A method as claimed in claim 1 comprising adjusting $U_{min}$ in increments $dU_{min}$ dependent on said measurement voltage U, such that when $U - dU_{min} < 0$, $U_{min}$ is decreased by $dU_{min}$, and after a predetermined time $U_{min}$ is increased by $dU_{min}$.

3. A method as claimed in claim 2 comprising calculating dU as a function of a difference between said measurement evoked current and said predetermined value.

4. A method as claimed in claim 1 comprising supplying blood in living tissue to said working electrode as said liquid medium, said blood containing oxygen as said chemical entity.

5. A method as claimed in claim 4 comprising adjusting a pacing rate for pacing a heart as a function of said difference $\Delta U = U - U_{min}$.

6. A method as claimed in claim 5 comprising calculating said rate adjustment according to a formula $K[(U - U_{min})/(U_{max} - U_{min})]$, wherein K is a factor limiting a highest rate increase, and $U_{max}$ is an adjustable value greater than U.

7. An apparatus for electrochemical determination of a concentration of at least one dissolved chemical entity in a liquid medium comprising:

a working electrode and a counter electrode, said working electrode being in contact with said liquid medium in which said at least one chemical entity is dissolved;

a voltage source for impressing a measurement voltage U on said working electrode relative to said counter electrode, said dissolved chemical entity reacting to said measurement voltage U by oxidation or reduction at said working electrode, resulting in production of a measurement evoked current;

a comparator which compares said measurement evoked current with a predetermined value;

an adjustment circuit for adjusting said measurement voltage U so that said measurement evoked current is substantially equal to said predetermined value so that said measurement evoked current is substantially constant;

a difference forming unit which forms a difference $\Delta U = U - U_{min}$ which corresponds to an oxidation/reduction reaction at said working electrode, wherein $U_{min}$ is a minimum voltage selected as a reference level; and an evaluation circuit for using said difference $\Delta U = U - U_{min}$ to calculate concentration variations of said chemical entity in said liquid.

8. A medical implant comprising:

a working electrode and a counter electrode, said working electrode being in contact with a liquid medium in which at least one chemical entity is dissolved, a voltage source for impressing a measurement voltage U on said working electrode relative to said counter electrode, said dissolved chemical entity reacting to said measurement voltage U by oxidation or reduction at said working electrode, resulting in production of a measurement evoked current, a comparator which compares said measurement evoked current with a predetermined value, an adjustment circuit for adjusting said measurement voltage U so that said measurement evoked current is substantially equal to said predetermined value so that said measurement evoked current is substantially constant, a difference forming unit which forms a difference $\Delta U = U - U_{min}$ which corresponds to an oxidation/reduction reaction at said working electrode, wherein $U_{min}$ is a minimum voltage selected as a reference level, an evaluation circuit for using said difference $\Delta U = U - U_{min}$ to calculate concentration variations of said chemical entity in said liquid; and a therapy administering unit which is supplied with said concentration variations calculated by said evaluation unit for administering a therapy dependent on said concentration variations.

9. A medical implant as claimed in claim 8 wherein said therapy administration unit is a pacemaker which administers pacing pulses having pacing parameters associated therewith which are varied dependent on said concentration variations.

* * * * *